US012336919B2

(12) United States Patent
Wulfman et al.

(10) Patent No.: US 12,336,919 B2
(45) Date of Patent: Jun. 24, 2025

(54) MEDICAL IMPLANTABLE DEVICES AND METHODS OF USING THE SAME

(71) Applicant: Boston Scientific Scimed Inc., Maple Grove, MN (US)

(72) Inventors: David Robert Wulfman, Minneapolis, MN (US); Danielle Frankson, Dayton, MN (US); Lauren Sfakis Lydecker, Millbury, MA (US); Joseph Thomas Delaney, Jr., Minneapolis, MN (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 405 days.

(21) Appl. No.: 17/700,310

(22) Filed: Mar. 21, 2022

(65) Prior Publication Data

US 2022/0296396 A1 Sep. 22, 2022

Related U.S. Application Data

(60) Provisional application No. 63/164,350, filed on Mar. 22, 2021.

(51) Int. Cl.
*A61F 2/04* (2013.01)
*A61F 2/00* (2006.01)
*A61F 2/06* (2013.01)
*A61F 2/848* (2013.01)
*A61F 2/90* (2013.01)
(Continued)

(52) U.S. Cl.
CPC ............ *A61F 2/848* (2013.01); *A61F 2/0077* (2013.01); *A61F 2210/0004* (2013.01); *A61F 2210/0076* (2013.01); *A61F 2240/001* (2013.01); *A61F 2250/001* (2013.01)

(58) Field of Classification Search
CPC ................... A61F 2/848; A61F 2/0077; A61F 2210/0004; A61F 2210/0076; A61F 2240/001; A61F 2250/001
See application file for complete search history.

(56) References Cited

U.S. PATENT DOCUMENTS 5,342,348 A * 8/1994 Kaplan ..................... A61F 2/91
606/198
5,639,278 A * 6/1997 Dereume .................. A61F 2/07
623/1.13
(Continued)

FOREIGN PATENT DOCUMENTS

CA 2621650 A1 * 3/2007 ............... A61F 2/91
CA 2905419 C * 4/2020 ............... A61F 2/86
(Continued)

OTHER PUBLICATIONS

International Search Report and Written Opinion issued on Jun. 29, 2022, in International Patent Application No. PCT/US2022/021215 (12 pages, in English).
(Continued)

*Primary Examiner* — Ann Hu
(74) *Attorney, Agent, or Firm* — Bookoff McAndrews PLLC

(57) ABSTRACT

A medical device that includes a body and a polymer matrix over the body. The polymer matrix includes a plurality of fibers defining a plurality of pores to permit tissue growth therethrough. The medical device includes a bio-adhesive coating at least partially covering the polymer matrix.

20 Claims, 3 Drawing Sheets

(51) Int. Cl.
*A61L 27/58* (2006.01)
*A61L 31/10* (2006.01)

(56) References Cited

U.S. PATENT DOCUMENTS

| | | | |
|---|---|---|---|
| 5,830,217 A | 11/1998 | Ryan | |
| 7,550,004 B2* | 6/2009 | Bahler | A61F 2/07 623/1.48 |
| 7,976,915 B2* | 7/2011 | Scheuermann | A61L 31/088 428/34.7 |
| 8,038,708 B2* | 10/2011 | Case | A61F 2/2475 623/1.24 |
| 8,574,615 B2* | 11/2013 | Tenney | A61P 41/00 424/423 |
| 8,585,753 B2* | 11/2013 | Scanlon | B29C 55/26 623/1.42 |
| 9,295,541 B2* | 3/2016 | Wagner | A61F 2/064 |
| 9,517,123 B2* | 12/2016 | Leewood | A61F 2/07 |
| 9,775,933 B2* | 10/2017 | Knisley | A61L 31/10 |
| 9,855,371 B2* | 1/2018 | Scanlon | A61L 31/14 |
| 9,867,690 B2* | 1/2018 | Soletti | A61F 2/062 |
| 9,993,582 B2* | 6/2018 | Hingston | A61L 31/10 |
| 10,076,406 B2* | 9/2018 | Blum | A61L 31/088 |
| 10,232,077 B2 | 3/2019 | Bender et al. | |
| 10,531,941 B2 | 1/2020 | Hynes et al. | |
| 10,736,730 B2* | 8/2020 | Hebert | A61B 17/12113 |
| 11,051,959 B2* | 7/2021 | Bar | C08G 79/04 |
| 11,304,831 B2* | 4/2022 | Nae | A61F 2/07 |
| 11,382,776 B2* | 7/2022 | Bluecher | A61F 2/848 |
| 11,684,498 B2* | 6/2023 | Spector | A61F 2/90 623/23.7 |
| 2002/0143384 A1* | 10/2002 | Ozasa | A61F 2/07 623/1.12 |
| 2003/0036794 A1* | 2/2003 | Ragheb | A61L 29/16 623/1.42 |
| 2003/0074049 A1* | 4/2003 | Hoganson | A61F 2/07 623/1.13 |
| 2008/0154351 A1* | 6/2008 | Leewood | A61F 2/89 606/139 |
| 2010/0298769 A1* | 11/2010 | Schewe | A61L 27/54 514/777 |
| 2011/0022149 A1* | 1/2011 | Cox | A61B 17/12177 623/1.11 |
| 2012/0245663 A1 | 9/2012 | Zarembo et al. | |
| 2013/0018448 A1* | 1/2013 | Folan | A61F 2/958 623/1.11 |
| 2014/0288632 A1* | 9/2014 | Soletti | A61L 27/34 623/1.13 |
| 2015/0045876 A1* | 2/2015 | Clerc | A61L 31/148 623/1.38 |
| 2016/0302911 A1* | 10/2016 | Soletti | A61F 2/062 |
| 2021/0252186 A1* | 8/2021 | Bahar | A61L 31/16 |
| 2021/0378849 A1* | 12/2021 | Richter | A61F 2/915 |
| 2023/0166008 A1* | 6/2023 | Rieth | A61F 29/06 623/1.11 |

FOREIGN PATENT DOCUMENTS

| | | |
|---|---|---|
| EP | 0938879 A2 * | 2/1999 |
| EP | 3030278 A1 | 6/2016 |
| WO | 2014065941 A1 | 5/2014 |

OTHER PUBLICATIONS

Vijayan, Amritha, et al. "PEG grafted chitosan scaffold for dual growth factor delivery for enhanced wound healing." Scientific reports 9.1 (2019): 1-12. (12 pages, in English).

Verdonk, René, et al. "Tissue ingrowth after implantation of a novel, biodegradable polyurethane scaffold for treatment of partial meniscal lesions." The American journal of sports medicine 39.4 (2011): 774-782. (6 pages).

* cited by examiner

MEDICAL IMPLANTABLE DEVICES AND METHODS OF USING THE SAME

CROSS-REFERENCE TO RELATED APPLICATIONS

This application claims the benefit of priority of U.S. Provisional Patent Application No. 63/164,350, filed Mar. 22, 2021, the entirety of which is incorporated herein by reference.

TECHNICAL FIELD

Various aspects of the present disclosure relate generally to medical implantation systems, devices, and related methods. For example, the present disclosure includes systems, devices, and related methods for fixating an implantable device to a target treatment site of a subject.

BACKGROUND

Medical devices designed for implantation in a subject, such as stents, may experience gradual migration from a target location within the subject at which the device was initially positioned. The migration tendencies of said medical devices may be caused by the compressible and/or flexible configurations of said devices, and influenced by peristalsis (e.g., involuntary constriction and relaxation of muscles of the esophagus, intestine, colon, etc.) or the generally lubricious environment of the target location. Movement of the implantable device may minimize the effectiveness of the device in treating the target location, and may cause further health complications for the subject. Some procedures may involve fixing the implantable device to the target location through use of ancillary tools, such as sutures or tape, to reduce migration. However, these approaches generally require subsequent removal of said ancillary tools from the target location, thereby necessitating the subject to undergo additional procedures. Devices and methods for fixing an implantable device within a subject without requiring use of ancillary tools to fix said device at the target location may be limited.

SUMMARY

Aspects of the present disclosure relate to, among other things, systems, devices, and methods for treating a target treatment site using an implantable device providing multiple fixation mechanisms. For example, the device may include a first, temporary fixation mechanism and a second, permanent fixation mechanism. Each of the aspects disclosed herein may include one or more of the features described in connection with any of the other disclosed aspects.

According to at least one example, a medical device includes a body; a polymer matrix over the body, wherein the polymer matrix comprises a plurality of fibers defining a plurality of pores to permit tissue growth therethrough; and a bio-adhesive coating at least partially covering the polymer matrix.

Any one of the medical devices described herein may include any of the following features. The bio-adhesive coating may be biodegradable. The plurality of fibers may have a diameter ranging from about 300 nm to about 700 nm. The bio-adhesive coating may be chemically bonded to the plurality of fibers. The body may include an expandable stent having a plurality of struts and a plurality of openings between adjacent struts, the plurality of fibers being positioned over the plurality of struts. The plurality of fibers may be electro-spun over the body. The medical device may include silicone between at least a portion of the body and the polymer matrix. The bio-adhesive coating may comprise a polysaccharide cross-linked with a linker molecule. The polysaccharide may comprise chitosan. The linker molecule may comprise polyethylene glycol. The polymer matrix may comprise a fluoropolymer. The body may comprise a bio-compatible metal or metal alloy configured to move from a compressed configuration to an expanded configuration. In the compressed configuration, for example, the body may have a first length and a first diameter, and in the expanded configuration, the body may have a second length greater than the first length and a second diameter smaller than the first diameter.

According to another example, the medical device includes an expandable body including a plurality of openings; a polymer matrix disposed along an exterior surface of the body and within at least a portion of the plurality of openings, wherein the polymer matrix comprises a plurality of fibers; and a bio-adhesive coating chemically bonded to the polymer matrix, wherein the bio-adhesive coating is biodegradable. The medical device may further include silicone between at least a portion of the body and the polymer matrix. The bio-adhesive coating may comprise chitosan. The chitosan may be cross-linked. The polymer matrix may comprise a thermoplastic polymer.

Methods of treatment are also disclosed For example, the method may include treating a subject by delivering a medical device to target tissue of the subject, wherein the medical device includes: an expandable body; a polymer matrix comprising a plurality of fibers over the body; and a bio-adhesive coating at least partially covering the polymer matrix; wherein the bio-adhesive coating adheres the polymer matrix and the body to the tissue; and wherein the medical device promotes cell growth from the tissue through the bio-adhesive coating and the polymer matrix. The bio-adhesive coating may maintain contact with the tissue, e.g., for 24 hours to 6 months.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary aspects of the disclosure and together with the description, serve to explain the principles of the disclosure.

DETAILED DESCRIPTION

Figure 1:
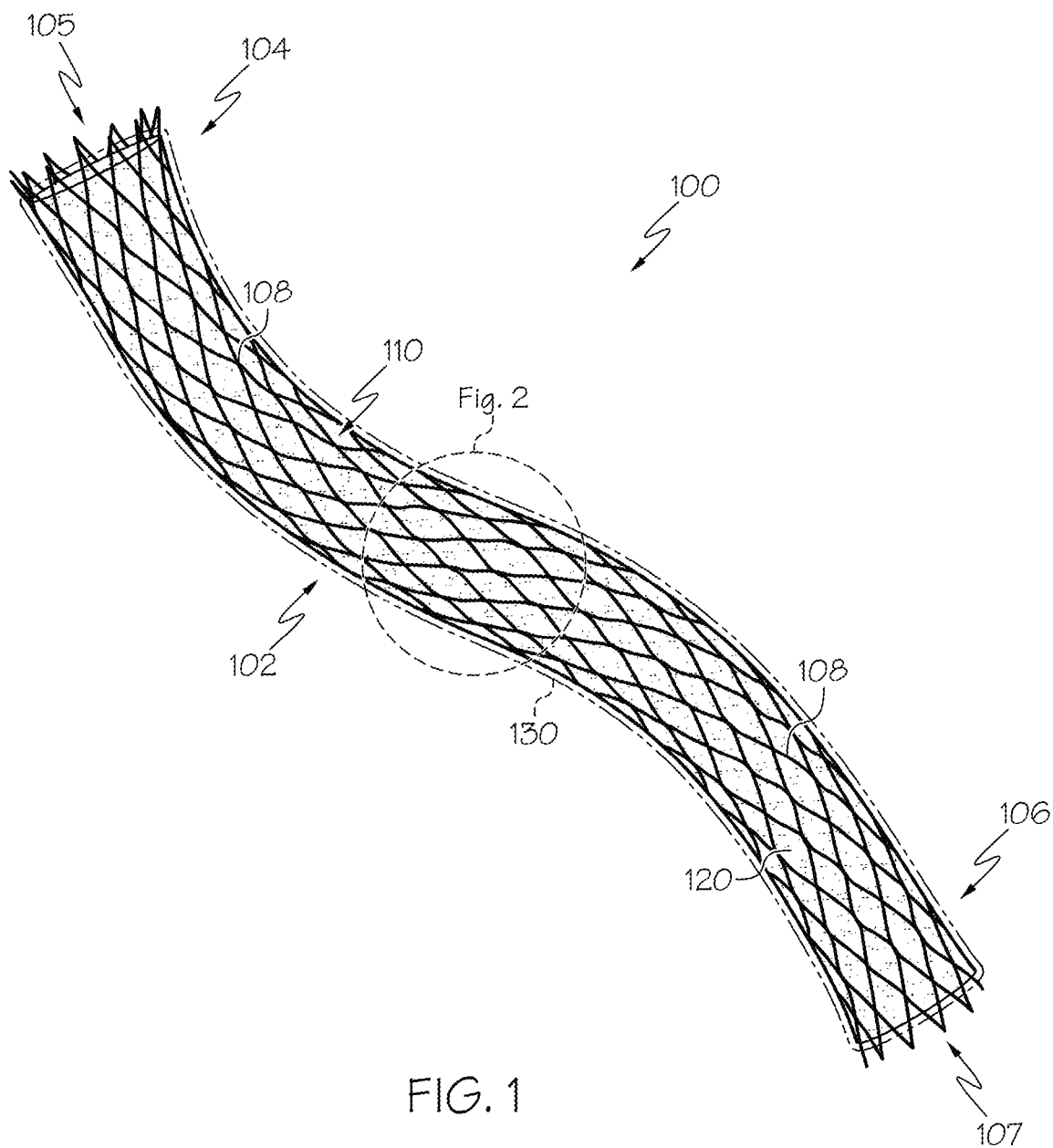
FIG. 1 is a perspective view of an exemplary medical device including a first and second fixation mechanism, according to aspects of this disclosure.

Implantable medical devices with features for facilitating attachment within a patient, e.g., to minimize migration of the device, are included herein. A target treatment site for placing the implantable medical device may include a tissue wall, such as an esophagus or other part of the gastrointestinal system of the patient. The devices herein may include features to inhibit migration from the initial, target treatment site at which the device was originally placed.

Examples of the disclosure include systems, devices, and methods for attaching an implantable medical device to a target treatment site within a subject (e.g., patient). In examples, accessing a patient's esophagus includes endoluminal placement of the medical device into the target treatment site. Placement of the medical device may be via a catheter, scope (endoscope, bronchoscope, colonoscope, etc.), tube, or sheath, inserted into an anatomical passageway via a natural orifice or via laparoscopy. The orifice can be, for example, the nose, mouth, or anus, and the placement can be in any portion of the GI tract, including the esophagus, stomach, duodenum, large intestine, or small intestine. Placement also can be in other organs or other bodily spaces reachable via the GI tract, other body lumens, or openings in the body, including via laparoscopy. This disclosure is not limited to any particular medical procedure or treatment site within a body.

Reference will now be made in detail to aspects of the disclosure, examples of which are illustrated in the accompanying drawings. Wherever possible, the same or similar reference numbers will be used through the drawings to refer to the same or like parts. The term "distal" refers to a portion farthest away from a user when introducing a device into a patient. By contrast, the term "proximal" refers to a portion closest to the user when placing the device into the subject. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal." As used herein, the terms "about," "substantially," and "approximately," indicate a range of values within +/−5% of a stated value.

Examples of the disclosure may relate to devices and methods for performing various medical procedures and/or treating portions of the large intestine (colon), small intestine, cecum, esophagus, any other portion of the gastrointestinal tract, and/or any other suitable patient anatomy (collectively referred to herein as a "target treatment site"). As mentioned above, this disclosure is not limited to any specific medical device or method, and aspects of the disclosure may be used in connection with any suitable medical tool and/or medical method, at any suitable site within the body. Various examples described herein include single-use or disposable medical devices.

FIG. 1 shows an exemplary medical device 100 in accordance with one or more examples of this disclosure. Medical device 100 comprises a body 102 having a longitudinal length defined between a first end 104 and a second end 106. One or more of first end 104 or second end 106 optionally may be flared radially outward relative to a cross-sectional profile of body 102. Body 102 may be flexible and configured to expand axially and/or radially when transitioning from a compressed configuration to an expanded configuration. Stated differently, body 102 may have a first length and a first diameter when in a first, compressed configuration. Body 102 may further have a second length and a second diameter when in a second, expanded configuration. The second length and/or the second diameter may be greater than the first length and/or the first diameter, respectively. Optionally, the second length may be greater than the first length and the second diameter may be greater than the first diameter.

Body 102 may include a lumen defined between first end 104 and second end 106, a first opening 105 at first end 104, and a second opening 107 at second end 106. First opening 105 and second opening 107 may be in fluid communication with one another through the lumen of body 102. As shown, body 102 includes an expandable stent assembly having a plurality of struts 108 and a plurality of openings 110 defined between adjacent struts 108. Body 102 may be formed of various suitable materials having flexible characteristics, including, for example, a biocompatible metal, a metal alloy, a shape memory material, etc. Medical device 100 may further include a biocompatible matrix 120 disposed over at least a portion of body 102 between first end 104 and second end 106, wherein matrix 120 may comprise one or more polymers. In some embodiments, polymer matrix 120 may be positioned over a substantial portion of the longitudinal length of body 102, such that polymer matrix 120 includes a longitudinal length that is substantially similar to body 102. In other embodiments, polymer matrix 120 may be positioned over a portion of body 102 that is less than the longitudinal length of body 102, such that one or more portions of body 102 are uncovered by polymer matrix 120.

Figure 2:
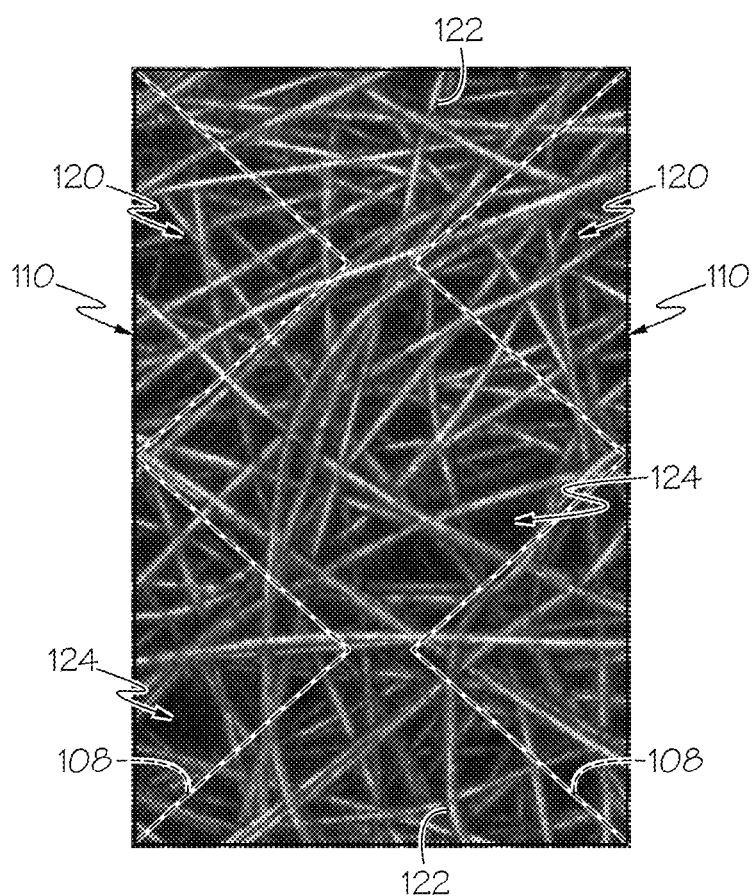
FIG. 2 is a partial enlarged view of the first and second fixation mechanisms of the medical device of FIG. 1, according to aspects of this disclosure.

As seen in FIG. 2, polymer matrix 120 may comprise a plurality of fibers 122 defining a plurality of pores 124 (e.g., interstices). The plurality of fibers 122 may be disposed over the plurality of struts 108 and the plurality of openings 110 of body 102, e.g., providing a porous matrix over body 102. Each fiber of the plurality of fibers 122 may have a diameter ranging from about 100 nanometers (nm) to about 900 nm, such as from about 300 nm to about 700 nm, about 230 nm to about 550 nm, or about 450 nm to about 650 nm. The thickness of polymer matrix 120 may range from at least 1 micron (μm) to at least one millimeter (mm), such as, e.g., from about 1.5 μm to about 850 μm, from about 5 μm to about 10 μm, from about 50 μm to about 250 μm, from about 350 μm to about 750 μm, from about 450 μm to about 600 μm, from about 650 μm to about 950 μm, or about 300 μm to about 550 μm. Each fiber 122 may have the same diameter, or the plurality of fibers 122 may include fibers of differing dimensions. It should be appreciated that the diameter(s) of the fibers 122 may be at least partially determinative of the size(s) of the pores 124 defined between adjacent fibers 122.

Being porous, polymer matrix 120 may allow passage of one or more materials through polymer matrix 120. For example, as described in further detail herein, polymer matrix 120 may permit tissue growth between the plurality of fibers 122 and through the plurality of pores 124. The dimensions of the plurality of pores 124 may at least partially determine a rate of tissue growth through polymer matrix 120. The dimensions (e.g., thickness, diameter, etc.) of the plurality of fibers 122 may at least partially determine the rate of tissue growth through polymer matrix 120. In some embodiments, the plurality of fibers 122 may be sintered to strengthen a material composition of the plurality of fibers 122 and reduce a friability of the polymer matrix 120. According to some examples herein, the porosity of polymer matrix 120 may remain substantially consistent when sintering the plurality of fibers 122. Further, for example, the porosity of polymer matrix 120 may be fine-tuned to allow for adequate degradation and cell growth infiltration between the plurality of fibers 122 and through the plurality of pores 124.

Polymer matrix 120 may be formed over body 102 by any suitable technique, including, for example, electrospinning. For example, a polymer material may be electro-spun over body 102 to form polymer matrix 120. Exemplary polymer materials include, but are not limited to, thermoplastic polymers, including fluoropolymers, which may be electro-spun while in liquid solution form. The material(s) may be delivered with high electrical forces such that the material(s) may be deposited over an exterior of body 102 in a randomized, asymmetrical, and/or irregular pattern. Solvent(s) in the liquid solution may evaporate and polymer chains form, e.g., becoming mechanically entangled. The resulting structure may comprise the plurality of fibers 122 deposited onto body 102. In some embodiments, polymer matrix 120 may comprise polyvinylidene fluoride, polyvinylidene difluoride (PVDF), and/or hexafluoropropylene (HFP).

As seen in FIG. 2, the plurality of fibers 122 may be intertwined with one another over the plurality of struts 108. It should be appreciated that the plurality of fibers 122 may be further intertwined with an exterior surface of body 102 to secure polymer matrix 120 to body 102. For example, medical device 100 may include a material between body 102 and the plurality of fibers 122, e.g., the material disposed as one or more outer layers along the exterior surface of body 102. The plurality of fibers 122 may comingle with the material of the outer layer(s). The outer layer(s) may comprise a polymer, such as, for example, silicone. Accordingly, during an electrospinning process of generating polymer matrix 120 over body 102, the material electro-spun onto body 102 (e.g., fluoropolymer) may be mechanically entangled with the outer layer.

The outer layer may be positioned between at least a portion of body 102 and polymer matrix 120. For example, silicone or other suitable polymer material of the outer layer(s) may be disposed within at least a portion of the plurality of openings 110 between the plurality of the struts 108, and the plurality of fibers 122 may be deposited over the plurality of struts 108 and/or the plurality of openings 110. To minimize constraining a flexibility of body 102, the plurality of fibers 122 may be concentrated over the plurality of struts 108 during the electrospinning process of polymer matrix 120. Further, the plurality of fibers 122 may be selectively guided over the plurality of struts 108 during the electrospinning process to preserve a profile of the plurality of openings 110 defined therebetween. With polymer matrix 120 formed along an exterior of body 102, polymer matrix 120 may provide and maintain a barrier about the lumen of body 102. As described in detail herein, polymer matrix 120 may provide a first, long-term (e.g., permanent) fixation mechanism for securing medical device 100 to a target treatment site within a subject.

Medical device 100 may further include a bio-adhesive coating 130 disposed over, and at least partially covering, polymer matrix 120. The bio-adhesive coating 130 may be chemically bonded to polymer matrix 120. Accordingly, polymer matrix 120 may be disposed between the bio-adhesive coating 130 and body 102 such that the bio-adhesive coating 130 is separated from body 102 by polymer matrix 120. The bio-adhesive coating 130 may comprise a biodegradable material, such that the bio-adhesive coating 130 may be resorbed or otherwise degrade after a period of time. As described in further detail herein, the bio-adhesive coating 130 may maintain contact with a target treatment site (e.g., tissue) for a desired amount of time, which may depend on chemical characteristics and/or the thickness of the bio-adhesive coating 130. For example, the bio-adhesive coating 130 may maintain contact with the target treatment site from approximately 24 hours to approximately 6 months, such as from about 3 days to about 1 week, from about 1 week to about 6 weeks, from about 1 month to about 3 months, or about 2 months to about 5 months. The degradation time may be controlled by various factors, including, for example, the nature of the biodegradable material and/or quantity (e.g., thickness) of the bio-adhesive coating 130 on polymer matrix 120. The thickness of bio-adhesive coating 130 over polymer matrix 120 may range from about at least 1 µm to at least 1 mm, such as, e.g., from about 1.5 µm to about 850 µm, from about 5 µm to about 10 µm, from about 50 µm to about 250 µm, from about 350 µm to about 750 µm, from about 450 µm to about 600 µm, from about 650 µm to about 950 µm, or about 300 µm to about 550 µm. Further, bio-adhesive coating 130 may be chemically modified on an exterior surface of polymer matrix 120.

Exemplary materials suitable for the bio-adhesive coating 130 include, but are not limited to, polysaccharides such as chitosan. The polysaccharide may be cross-linked with a linker molecule. Such linker molecules include, for example, polyethylene glycol (PEG). PEG may provide a hydrophilic scaffold along polymer matrix 120, and may serve as an anchor for bio-adhesive coating 130 to attach to polymer matrix 120. The hydrophilic properties of PEG may provide adhesive capabilities for securing bio-adhesive coating 130 to polymer matrix 120. Other suitable materials for bio-adhesive coating 130 may include, but are not limited to, polymers such as chitosan optionally modified with thiol groups, PEG modified with thiol groups, and oxidized cellulose. The bio-adhesive coating 130 may have hemostatic properties for simulating a healing response from a target treatment site (e.g., tissue) when in contact thereto. Stated differently, the bio-adhesive coating 130 may treat injuries at the target treatment site, such as wounds, hemorrhages, damaged tissues, bleeding, etc. The bio-adhesive coating 130 may serve as a wound dressing to inhibit excessive bleeding and/or promote rapid healing. Additionally, the bio-adhesive coating 130 may have adhesion characteristics capable of securing body 102 to the target treatment site.

As mentioned above, the bio-adhesive coating 130 may be chemically bonded to the polymer matrix 120, including via the linker molecule. Accordingly, the linker molecule (e.g., PEG) may be cross-linked with the plurality of fibers 122 to facilitate a connection between the bio-adhesive coating 130 and polymer matrix 120. In some examples, the linker molecule may become entangled with the polymer chains of polymer matrix 120 as the plurality of fibers 122 are formed on body 102. In some examples, the bio-adhesive coating 130 may be prepared using plasma to cross-link the polysaccharide and linker molecule. As described in detail herein, the bio-adhesive coating 130 may provide a second, temporary fixation mechanism for securing medical device 100 to a target treatment site within a subject.

According to some aspects of the present disclosure, the plurality of fibers 122 may be selectively deposited over body 102 to control a fixation characteristic of medical device 100 to a target treatment site. For example, the plurality of fibers 122 may be deposited along one or more regions of body 102, thereby controlling an area of tissue ingrowth into medical device 100 to the one or more specific regions. As discussed above, the bio-adhesive coating 130 may adhere to a surface area of polymer matrix 120, such that medical device 100 may include the bio-adhesive coating 130 along the one or more regions of body 102 when the plurality of fibers 122 are selectively deposited thereon.

Figure 3:
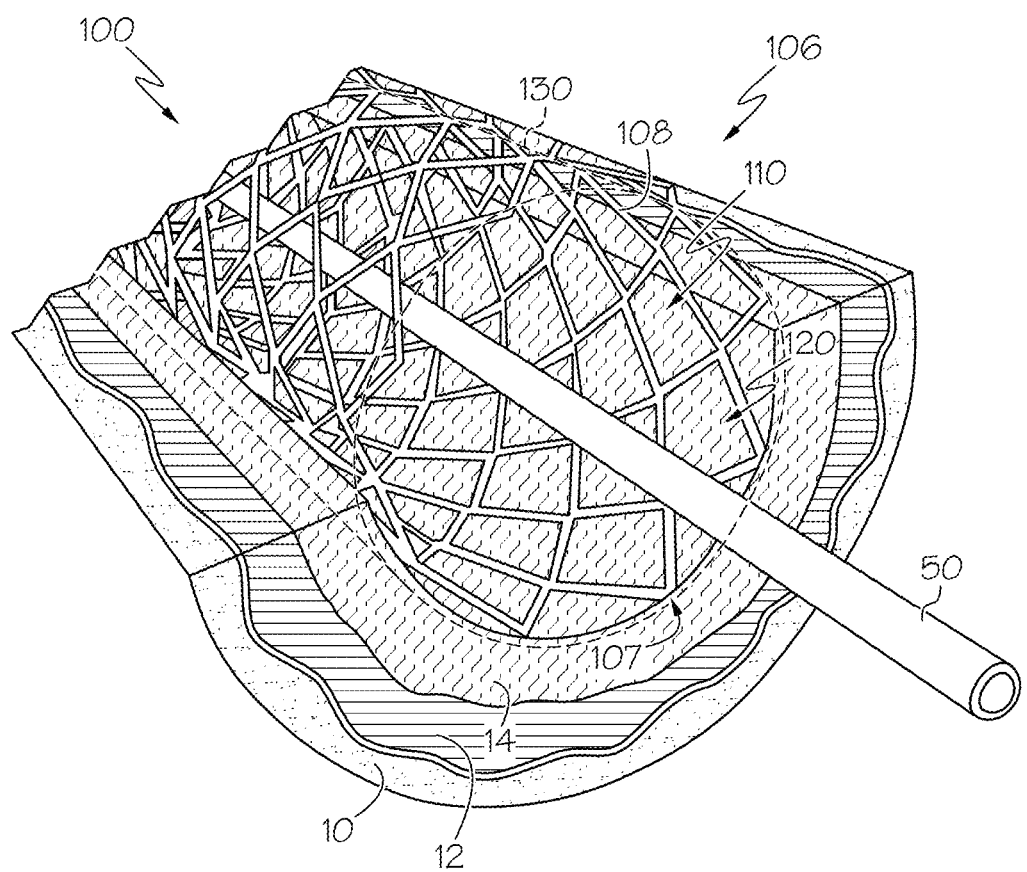
FIG. 3 is a partial perspective view of the medical device of FIG. 1 anchored against a target treatment site, according to aspects of this disclosure.

Referring now to FIG. 3, an exemplary use of medical device 100 to treat a target treatment site (e.g., tissue) within a subject is depicted. It should be understood that medical device 100 may be positioned at the target treatment site through use of a medical instrument (e.g., an endoscope) that is inserted through the subject's body and navigated toward the target treatment site. It should be understood that medical device 100 of this disclosure may be used in various locations (target treatment sites) within a subject's body, including but not limited to, the gastrointestinal tract, an organ, or other tissue. In the example depicted in FIG. 3, the target treatment site includes a tissue wall 12 within a subject's body 10, and the tissue wall 12 has a mucous layer 14 disposed along an exterior of the tissue wall 12. According to some examples herein, the bio-adhesive coating 130 of medical device 100 may have a positive charge, complementary to a negative charge of the mucous layer 14.

Upon reaching the tissue wall 12, medical device 100 may be inserted transluminally through medical instrument and deployed therefrom at the tissue wall 12. One or more tools 50 may be received through the lumen of the body 102 to facilitate navigation of medical device 100 toward the tissue wall 12, such as, for example, a guidewire. In some embodiments, the bio-adhesive coating 130 may provide a smooth, outer atraumatic surface to facilitate passage of medical device 100 through the subject 10 and/or inhibit injury to the tissue wall 12 by the polymer matrix 120 and/or body 102. Medical device 100 may be pressed against the tissue wall 12 such that the bio-adhesive coating 130 contacts the mucous layer 14. With body 102 having a flexible configuration, medical device 100 may conform to a profile of the tissue wall 12.

With the bio-adhesive coating 130 being positively charged and the mucous layer 14 being negatively charged, the bio-adhesive coating 130 may be attracted to the mucous layer 14 and form chemical bonds with the tissue surface, thereby anchoring medical device 100 to the tissue wall 12. The bio-adhesive coating 130 may maintain medical device 100 against the tissue wall 12 for at least a minimum duration until the bio-adhesive coating 130 is resorbed or otherwise degrades. Accordingly, the bio-adhesive coating 130 may serve a tissue adhesive mechanism for temporarily fixing medical device 100 to the tissue wall 12, and inhibiting migration of medical device 100 from the target treatment site. Further, the bio-adhesive coating 130 may further promote healing of the tissue wall 12 via the hemostatic properties of the bio-adhesive coating 130 while the bio-adhesive coating 130 remains in contact with the tissue wall 12.

Still referring to FIG. 3, as the bio-adhesive coating 130 adheres medical device 100 to the mucous layer 14, the bio-adhesive coating 130 may facilitate tissue growth from the tissue wall 12 through polymer matrix 120. Stated differently, by maintaining polymer matrix 120 within close proximity to the tissue wall 12, the bio-adhesive coating 130 may allow tissue cells from the tissue wall 12 to grow through the bio-adhesive coating 130 and into the plurality of pores 124. The tissue cells may become intertwined with the plurality of fibers 122, thereby anchoring medical device 100 to the tissue wall 12 and inhibiting migration of medical device 100 from the target treatment site. In other words, the plurality of pores 124 may serve as sites that permit tissue growth into polymer matrix 120. The bio-adhesive coating 130 may maintain medical device 100 against the tissue wall 14 via bonding with the mucous layer 14, to thereby allow the tissue cells sufficient time to grow through polymer matrix 120.

As described further above, the size(s) of the plurality of pores 124 may at least partially control the rate of tissue cell growth through polymer matrix 120, and the diameter(s) of the plurality of fibers 122 may at least partially determine the size(s) of the plurality of pores 124. Further, the diameter(s) of the plurality of fibers 122 may correspond or correlate to a minimum required force for disengaging medical device 100 from a target treatment site. Stated differently, the plurality of fibers 122 may be sized and/or shaped to provide medical device 100 sufficient mechanical strength in inhibiting migration of medical device 100 from the target treatment site. For example, a minimum extraction force sufficient to move medical device 100 relative to the target treatment site may be at least partially associated with a size and/or shape of the plurality of fibers 122. Accordingly, the diameter of the plurality of fibers 122 may at least partially contribute to inhibiting the unintentional release of medical device 100 from the tissue wall 12.

Still referring to FIG. 3, upon degradation of the bio-adhesive coating 130, medical device 100 may remain anchored to the tissue wall 12 via an engagement of polymer matrix 120 to the tissue wall 12. Accordingly, despite removal of the bio-adhesive coating 130 from between polymer matrix 120 and the tissue wall 12, polymer matrix 120 and body 102 may remain attached to the tissue wall 12 in response to the tissue cell growth through polymer matrix 120. Medical device 100 may be designed to treat strictures in a body lumen defined by the tissue wall 12, and/or provide a fluid pathway for material (e.g., fluid, digested material, etc.) to flow through body 102 following an invasive medical procedure. By providing a physical barrier between body 102 and the tissue wall 12, polymer matrix 120 may ensure a fluid pathway through body 102 is preserved. Further, polymer matrix 120 may facilitate removal of medical device 100 upon completion of a procedure. For instance, polymer matrix 120 may reduce a surface area of body 102 which may be anchored to the tissue wall 12, thereby allowing medical device 100 to be removed from the subject 10 upon applying an application of force thereto. Further, for example, the thickness of medical device 100 including the thickness of polymer matrix 120 and an exposed portion of the plurality of fibers 122 may facilitate removal of medical device 100 from the subject 10. Additionally, polymer matrix 120 may control an extent (e.g., depth) and/or degree of tissue ingrowth into medical device 100, providing further control for the removal of medical device 100 upon completion of a procedure.

Each of the aforementioned systems, devices, assemblies, and methods may be used to secure an implantable device to target tissue with an enhanced degree fixation. By providing a medical device with temporary and permanent mechanisms capable of fixing the medical device to the target tissue, instances of the device migrating from the target site may be minimized, thereby increasing an effectiveness in treating the target site. In this instance, a user may reduce overall procedure time, increase efficiency of procedures, and/or avoid unnecessary harm to a subject's body caused by subsequent procedures to reposition the device at the target site due to migration of the device.

It will be apparent to those skilled in the art that various modifications and variations may be made in the disclosed devices and methods without departing from the scope of the disclosure. Other aspects of the disclosure will be apparent to those skilled in the art from consideration of the specification and practice of the features disclosed herein. It is intended that the specification and examples be considered as exemplary only.

What is claimed is:

1. A medical device, comprising:
    a body that includes an expandable stent having a plurality of struts and a plurality of openings between adjacent struts of the plurality of struts;
    a polymer matrix over the body, wherein the polymer matrix comprises a plurality of fibers defining a plurality of pores to permit tissue growth therethrough;
    silicone disposed at least partially within the plurality of openings of the body and disposed radially between the body and the polymer matrix; and
    a bio-adhesive coating at least partially covering the polymer matrix.

2. The medical device of claim 1, wherein the bio-adhesive coating is biodegradable.

3. The medical device of claim 1, wherein each of the plurality of fibers has a diameter ranging from about 300 nm to about 700 nm.

4. The medical device of claim 1, wherein the bio-adhesive coating is chemically bonded to the plurality of fibers.

5. The medical device of claim 1, wherein the plurality of fibers are electro-spun over the body.

6. The medical device of claim 1, wherein the bio-adhesive coating comprises a polysaccharide cross-linked with a linker molecule.

7. The medical device of claim 6, wherein the polysaccharide comprises chitosan.

8. The medical device of claim 6, wherein the linker molecule comprises polyethylene glycol.

9. The medical device of claim 1, wherein the polymer matrix comprises a fluoropolymer.

10. The medical device of claim 1, wherein the body comprises a biocompatible metal or metal alloy configured to move from a compressed configuration to an expanded configuration.

11. The medical device of claim 10, wherein in the compressed configuration, the body has a first length and a first diameter, and in the expanded configuration, the body has a second length greater than the first length and a second diameter smaller than the first diameter.

12. The medical device of claim 1, wherein the body has a first end and a second end and a longitudinal length defined therebetween, and wherein the polymer matrix is positioned over the body such that a longitudinal length of the polymer matrix is substantially similar to the longitudinal length of the body.

13. A medical device, comprising:
    an expandable body including a plurality of struts, and a plurality of openings defined between adjacent struts of the plurality of struts;
    a polymer matrix disposed along an exterior surface of the body, wherein the polymer matrix comprises a plurality of fibers that are electro-spun over the plurality of struts;
    silicone disposed at least partially within the plurality of openings and between the body and the polymer matrix, wherein the plurality of fibers are mechanically entangled with the silicone, wherein the silicone is disposed radially between the plurality of fibers and the plurality of struts; and
    a bio-adhesive coating chemically bonded to the polymer matrix, wherein the bio-adhesive coating is biodegradable, wherein the bio-adhesive coating comprises a polysaccharide cross-linked with a linker molecule, wherein the polysaccharide comprises chitosan and wherein the linker molecule comprises polyethylene glycol.

14. The medical device of claim 13, wherein the polymer matrix comprises a thermoplastic polymer.

15. The medical device of claim 13, wherein the bio-adhesive coating is negatively charged.

16. The medical device of claim 13, wherein each of the plurality of fibers has a diameter ranging from about 300 nm to about 700 nm, and wherein at least one of the plurality of fibers has a different diameter relative to at least another one of the plurality of fibers.

17. The medical device of claim 16, wherein the plurality of fibers define a plurality of pores to permit tissue growth therethrough, and wherein at least one of the plurality of pores has a diameter different relative to a diameter of at least another one of the plurality of pores.

18. A method of treating a subject, comprising:
    delivering a medical device to target tissue of the subject, wherein the medical device comprises:
        an expandable body including a plurality of struts and a plurality of openings between adjacent struts of the plurality of struts;
        a polymer matrix comprising a plurality of fibers over the body;
        silicone disposed at least partially within the plurality of openings of the body and disposed radially between the body and the polymer matrix, wherein the plurality of fibers are electro-spun over the body and mechanically entangled with the silicone; and
        a bio-adhesive coating at least partially covering the polymer matrix;
    wherein the bio-adhesive coating adheres the polymer matrix and the body to the tissue; and
    wherein the medical device promotes cell growth from the tissue through the bio-adhesive coating and the polymer matrix.

19. The method of claim 18, wherein the bio-adhesive coating maintains contact with the tissue for 24 hours to 6 months.

20. The medical device of claim 19, wherein the bio-adhesive coating comprises a polysaccharide cross-linked with a linker molecule, wherein the polysaccharide comprises chitosan and wherein the linker molecule comprises polyethylene glycol.

* * * * *